United States Patent
Nishihara

(10) Patent No.: US 9,502,273 B2
(45) Date of Patent: Nov. 22, 2016

(54) HEAT TREATMENT APPARATUS AND HEAT TREATMENT METHOD FOR MEASURING PARTICLE CONCENTRATION

(71) Applicant: DAINIPPON SCREEN MFG. CO., LTD., Kyoto (JP)

(72) Inventor: Hideo Nishihara, Kyoto (JP)

(73) Assignee: SCREEN Holdings Co., Ltd., Kyoto (JP)

( * ) Notice: Subject to any disclaimer, the term of this patent is extended or adjusted under 35 U.S.C. 154(b) by 651 days.

(21) Appl. No.: 13/895,540

(22) Filed: May 16, 2013

(65) Prior Publication Data

US 2013/0315576 A1    Nov. 28, 2013

(30) Foreign Application Priority Data

May 23, 2012   (JP) ................ 2012-117475
Mar. 26, 2013   (JP) ................ 2013-063384

(51) Int. Cl.
| | |
|---|---|
| F27D 11/00 | (2006.01) |
| H01L 21/67 | (2006.01) |
| G01N 15/00 | (2006.01) |
| G01N 15/06 | (2006.01) |
| G01N 15/14 | (2006.01) |

(52) U.S. Cl.
CPC ........ H01L 21/67115 (2013.01); G01N 15/00 (2013.01); G01N 15/06 (2013.01); H01L 21/67253 (2013.01); G01N 2015/1486 (2013.01)

(58) Field of Classification Search
CPC ............. H01L 21/67115; H01L 21/67253; G01N 15/00; G01N 15/06; G01N 2015/1486
USPC ............. 219/405; 392/416; 438/5, 689, 708
See application file for complete search history.

(56) References Cited

U.S. PATENT DOCUMENTS

| | | | | |
|---|---|---|---|---|
| 4,928,537 | A * | 5/1990 | Liu et al. ............. | G01N 1/2202 377/10 |
| 5,468,296 | A * | 11/1995 | Patrick et al. ........ | C23C 16/507 118/726 I |
| 7,068,926 | B2 | 6/2006 | Nozaki ................ | 392/416 |
| 2003/0040193 | A1 * | 2/2003 | Bailey et al. ......... | B08B 7/00 438/710 |
| 2009/0299652 | A1 * | 12/2009 | Nakayama ........ | H01L 21/67069 702/26 |

FOREIGN PATENT DOCUMENTS

| | | |
|---|---|---|
| JP | 07-230954 | 8/1995 |
| JP | 07-321046 | 12/1995 |
| JP | 09-017705 | 1/1997 |
| JP | 2005-072291 | 3/2005 |

* cited by examiner

*Primary Examiner* — Thien S Tran
(74) *Attorney, Agent, or Firm* — Ostrolenk Faber LLP

(57) ABSTRACT

A heat treatment apparatus includes a chamber for receiving a substrate therein, and a measurement part for measuring an air particle concentration in a processing space provided in the chamber. An air particle concentration in the processing space provided in the chamber is measured by the measurement part. The air particle concentration is correlated with the number of particles attached to a substrate received in the chamber. Accordingly, by conducting a particle test after the air particle concentration in the processing space is lowered to an air particle concentration corresponding to the number of particles existing on the substrate which can pass the particle test, the number of times the particle test should be conducted after maintenance of the heat treatment apparatus can be reduced.

4 Claims, 12 Drawing Sheets

F I G. 3
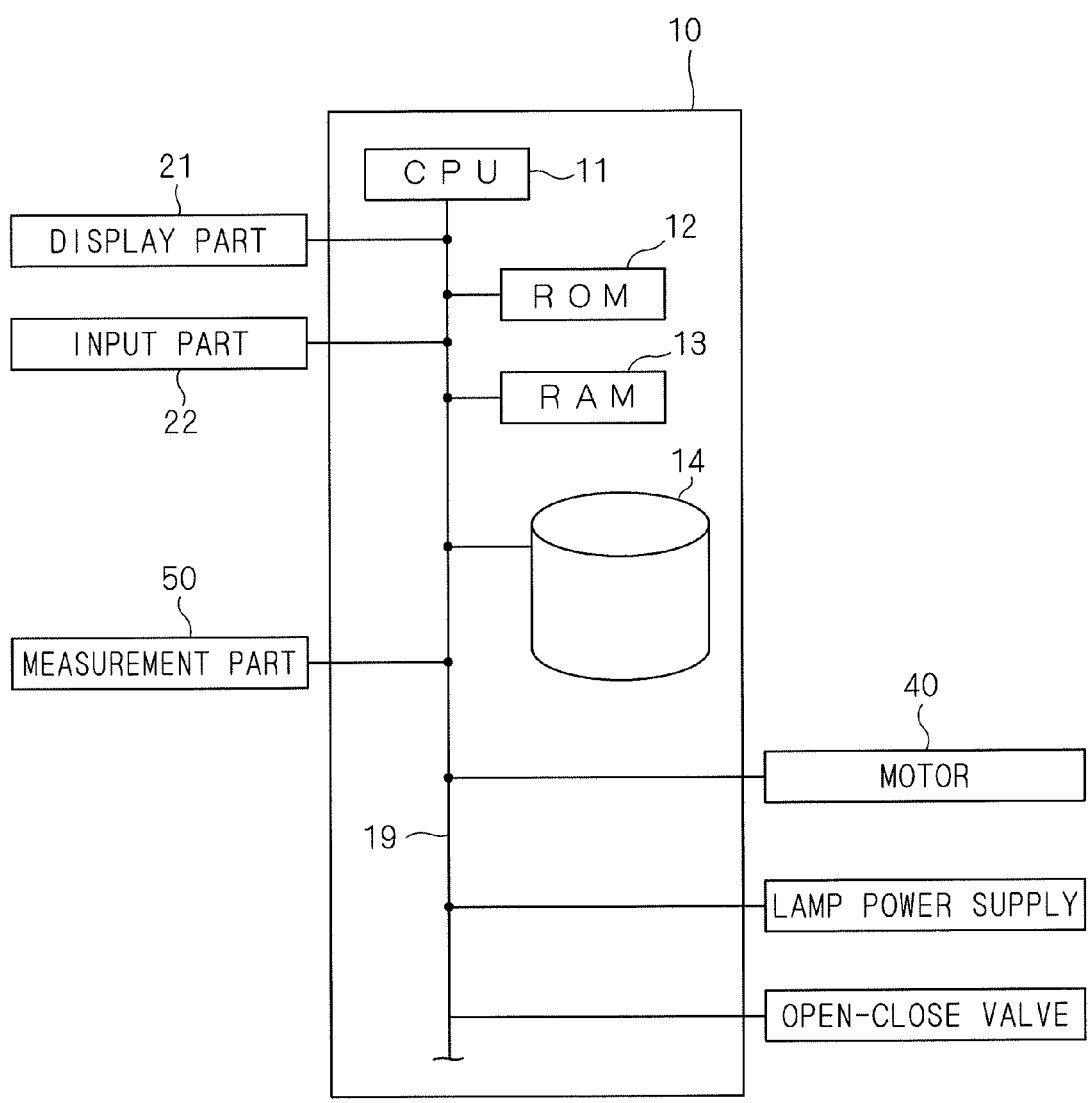

F I G . 8
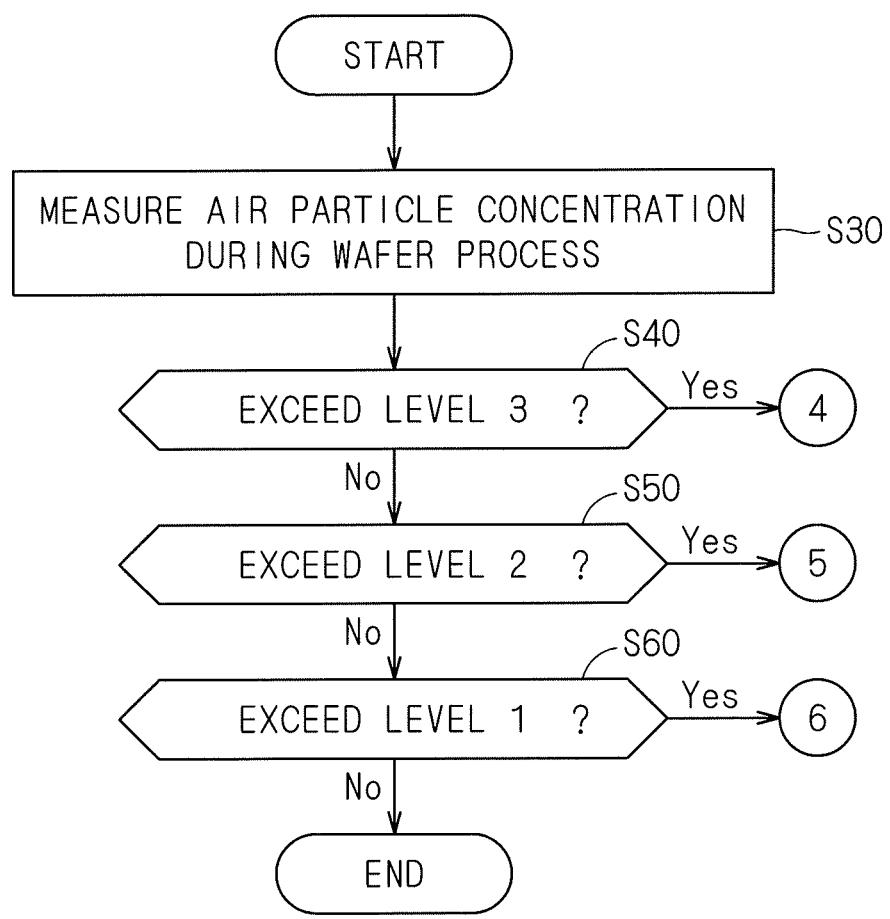

F I G . 9
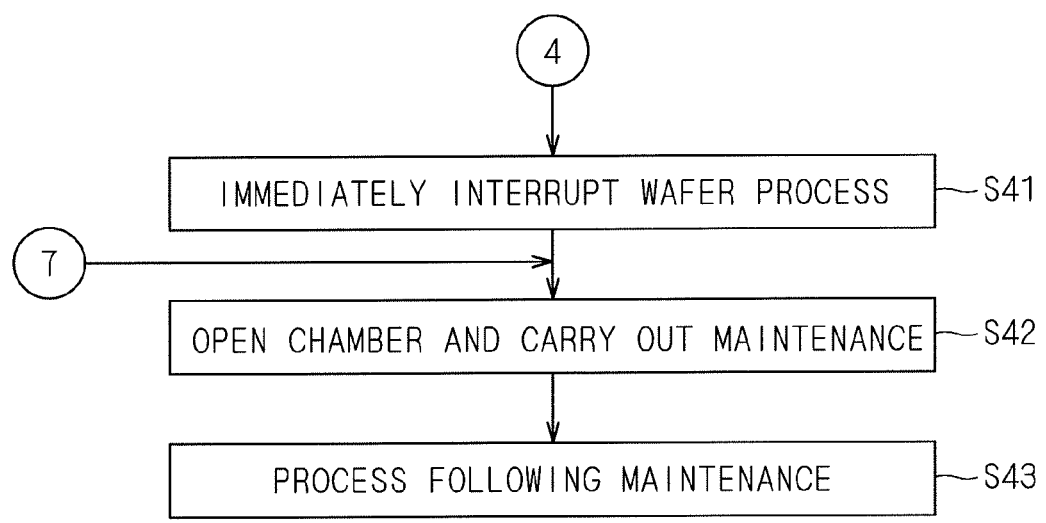

HEAT TREATMENT APPARATUS AND HEAT TREATMENT METHOD FOR MEASURING PARTICLE CONCENTRATION

BACKGROUND OF THE INVENTION

Field of the Invention

The present invention relates to a heat treatment technology for heating a semiconductor wafer, a glass substrate, or the like, (hereinafter, simply referred to as "substrate") that is placed in a process chamber.

Description of the Background Art

As well known, a semiconductor component or the like is manufactured through a large number of process steps, and various manufacturing apparatuses corresponding to the respective process steps are used. Many of the apparatuses are each provided with a cleaning mechanism therein because the manufacture of the semiconductor component or the like, which is becoming finer and finer, requires an ultraclean atmosphere. For example, Japanese Patent Application Laid-Open No. 7-321046 (1995) discloses a technique that causes an ozone gas to flow under ultraviolet irradiation, to thereby remove an organic substance existing on a substrate. Japanese Patent Application Laid-Open No. 9-17705 (1997) discloses a technique in which an unnecessary film attached to a surface of an inner wall of a process chamber or to a surface of a structure inside the process chamber is cleaned away at about 200° C. with a supply of a $ClF_3$ gas thereto. Japanese Patent Application Laid-Open No. 7-230954 (1995) discloses a cleaning technique in which, in a plasma processing apparatus, a residual material attached to a surface of a structural component inside a chamber (process chamber) is heated and thereby decomposed and removed.

Steps for manufacturing a semiconductor component or the like include an ion implantation step of implanting ions of boron, arsenic, or the like, into a silicon wafer (substrate). For the purpose of activating the ions implanted in the substrate, a heat treatment is performed. The heat treatment for activating ions is implemented by heating (annealing) the substrate to a temperature of, for example, about 1000° C. to 1100° C.

In a heat treatment apparatus that performs such a heat treatment, a fault such as a defect or cracking may occur in the substrate due to the heat treatment. For example, in flash annealing that is a heat treatment using flash lamps, the substrate may be broken and a shape fault such as a defect or cracking may occur in the substrate because of an impact caused by instantaneous radiation of light with an enormous amount of energy at a time of flash heating or because the substrate is moved up by a quartz-made arm having a temperature lower than the heat-treated substrate.

A breakage of the substrate causes a large amount of particles in the process chamber due to broken pieces of the substrate itself, damage to peripheral structures, and the like. When a breakage of the substrate occurs, needless to say, the process chamber is opened and maintenance is carried out, for the collection of the broken pieces and the like. However, it is very difficult to completely remove the caused particles. Additionally, opening the process chamber undesirably allows particles existing outside to be newly taken into the process chamber. When the flash heating treatment is performed under a state where particles remain in the process chamber, the particles are attached to the substrate and cause a process fault.

Conventionally, therefore, a method has been adopted in which, after the process chamber is opened and the maintenance is carried out, the flash heating is performed on a dummy wafer to thereby attach particles to the dummy wafer, and the particles are removed. In more detail, in this method, a particle removal process and a comparison and examination process ("particle test") are repeated until a measurement result of the particle test becomes equal to or less than a predetermined allowable value. In the particle removal process, particles are attached to the dummy wafer by means of the flash heating. In the comparison and examination process, the dummy wafer is taken out from the process chamber and transported into a measuring apparatus that is separately provided and configured to measure the number of particles attached onto the wafer. Then, the number of particles attached to the dummy wafer is measured, and the measurement result is compared and examined against the predetermined allowable value. However, to reach a state where the measurement result of the particle test is equal to or less than the predetermined allowable value, normally, it is necessary to repeat the particle removal process and the particle test a considerable number of times. Moreover, it is normally not easy to perform the particle test in, for example, a user's manufacturing plant in which the heat treatment apparatus is installed. Accordingly, a cleaning process for cleaning the inside of the process chamber after the maintenance requires a considerable number of dummy wafers and a process time, which causes a problem of a large cost increase.

Therefore, in a heat treatment apparatus disclosed in U.S. Pat. No. 7,068,926, a method is adopted in which a particle removal process for removing particles existing in a process chamber is implemented by repeating emission of flashes of light in an empty process chamber having no wafer, to thereby cause particles to scatter within the process chamber, and then exhausting the process chamber. In this method, when the number of times of emission of flashes of light, which is repeated at predetermined time intervals, reaches a predetermined value, it is determined that the number of particles in the process chamber becomes equal to or less than an allowable limit. Thus, the emission of flashes of light process is stopped. Then, similarly to the conventional method, the particle test is performed by actually using a dummy wafer. Based on a result of the particle test, whether or not the cleaning process for cleaning the inside of the process chamber is completed is determined.

However, in the apparatus disclosed in U.S. Pat. No. 7,068,926, it is determined that the number of particles existing in the process chamber becomes equal to or less than the allowable limit, based on the fact that the number of times the flash heating is performed in the empty process chamber reaches a predetermined value. Accordingly, in a case where the number of particles in the process chamber is larger than assumed, the particle test using the dummy wafer is performed under a state where the inside of the process chamber has not been sufficiently cleaned. As a result, the particle removal process using the flash heating and the particle test using the dummy wafer have to be performed again. In this manner, the apparatus disclosed in U.S. Pat. No. 7,068,926 still involves a problem that repetition of the particle test may result in the need for a considerable number of dummy wafers and a process time.

Moreover, conventionally, a situation sometimes occurs in which, in the course of continuously performing the heat treatment on a lot including a plurality of substrates, the degree of cleanliness in the process chamber rapidly deteriorates. A conceivable cause of the deterioration in the degree of cleanliness is, for example, the bringing-in of particles by the substrates or a trouble occurring in a gas supply and exhaust system for supplying and exhausting a gas to and out of the process chamber. Here, in the conventional heat treatment apparatus, even though the degree of cleanliness in the process chamber deteriorates during the process, detection thereof is difficult. Thus, the deterioration cannot be promptly responded to, and there is a fear that a large number of mis-processed substrates may be produced. Additionally, in a case where the degree of cleanliness in the process chamber deteriorates during the process, it is necessary to open the process chamber and carry out the maintenance. This causes a problem of a prolonged downtime.

SUMMARY OF THE INVENTION

The present invention is directed to a heat treatment apparatus for heating a substrate.

In an aspect of the present invention, a heat treatment apparatus includes: a process chamber for receiving a substrate therein; and a measurement part for measuring an air particle concentration in a processing space provided in said process chamber.

The air particle concentration is correlated with the number of particles attached to a substrate received in the process chamber. Accordingly, by conducting a particle test after the air particle concentration in the processing space is lowered to an air particle concentration corresponding to the number of particles existing on the substrate which can pass the particle test, the number of times the particle test should be conducted after maintenance of the heat treatment apparatus can be reduced.

The present invention is also directed to a particle measurement method for measuring the number of particles attached to a substrate received in a process chamber of a heat treatment apparatus.

In an aspect of the present invention, a particle measurement method includes the steps of: (a) obtaining correlation information that indicates the correlation between an air particle concentration in a processing space provided in the process chamber and the number of particles attached to a substrate received in the process chamber; (b) measuring an air particle concentration in the processing space; and (c) based on the air particle concentration obtained as a result of the measurement in the step (b) and the correlation information, calculating the number of particles that will be attached to a substrate intended to be received in the process chamber.

By conducting a particle test after the air particle concentration in the processing space is lowered to an air particle concentration corresponding to the number of particles existing on the substrate which can pass the particle test, the number of times the particle test should be conducted after maintenance of the heat treatment apparatus can be reduced.

The present invention is further directed to a heat treatment method for heating a substrate.

In an aspect of the present invention, a heat treatment method includes the steps of: (a) causing a substrate to be received in a process chamber; (b) heating the substrate in the process chamber; (c) measuring an air particle concentration in a processing space provided in the process chamber during the step (b); and (d) in a case where the air particle concentration obtained as a result of the measurement in the step (c) exceeds a predetermined threshold value, removing particles existing in the process chamber.

When the air particle concentration obtained as a result of the measurement exceeds the predetermined threshold value, particles existing in the process chamber are removed. Accordingly, even when the particle concentration in the process chamber increases during the process of the substrate, the number of particles can be promptly reduced.

Preferably, in an aspect of the present invention, in a case where the air particle concentration obtained as a result of the measurement in the step (c) exceeds a first threshold value, in the step (d), particles existing in the process chamber are removed with a maximum flow rate of the supply and exhaust to and out of the process chamber.

Preferably, in an aspect of the present invention, in a case where the air particle concentration obtained as a result of the measurement in the step (c) exceeds a second threshold value that is greater than the first threshold value, in the step (d), particles existing in the process chamber are removed while a substrate is being imaginarily transported.

Preferably, in an aspect of the present invention, in a case where the air particle concentration obtained as a result of the measurement in the step (c) exceeds a third threshold value that is greater than the second threshold value, in the step (d), the process chamber is opened and maintenance is carried out.

Therefore, an object of the present invention is to reduce the number of times the particle test should be conducted after the maintenance.

Another object of the present invention is to promptly reduce the number of particles even when the particle concentration in the process chamber increases during the process of the substrate.

These and other objects, features, aspects and advantages of the present invention will become more apparent from the following detailed description of the present invention when taken in conjunction with the accompanying drawings.

BRIEF DESCRIPTION OF THE DRAWING

FIG. 3 is a block diagram showing a configuration of a controller of the heat treatment apparatus shown in FIG. 1;

FIG. 8 is a flowchart of a process in a heat treatment apparatus according to a second preferred embodiment;

FIG. 9 is a flowchart showing procedures taken when the air particle concentration exceeds a level 3;

DESCRIPTION OF THE PREFERRED EMBODIMENTS

Figure 1:
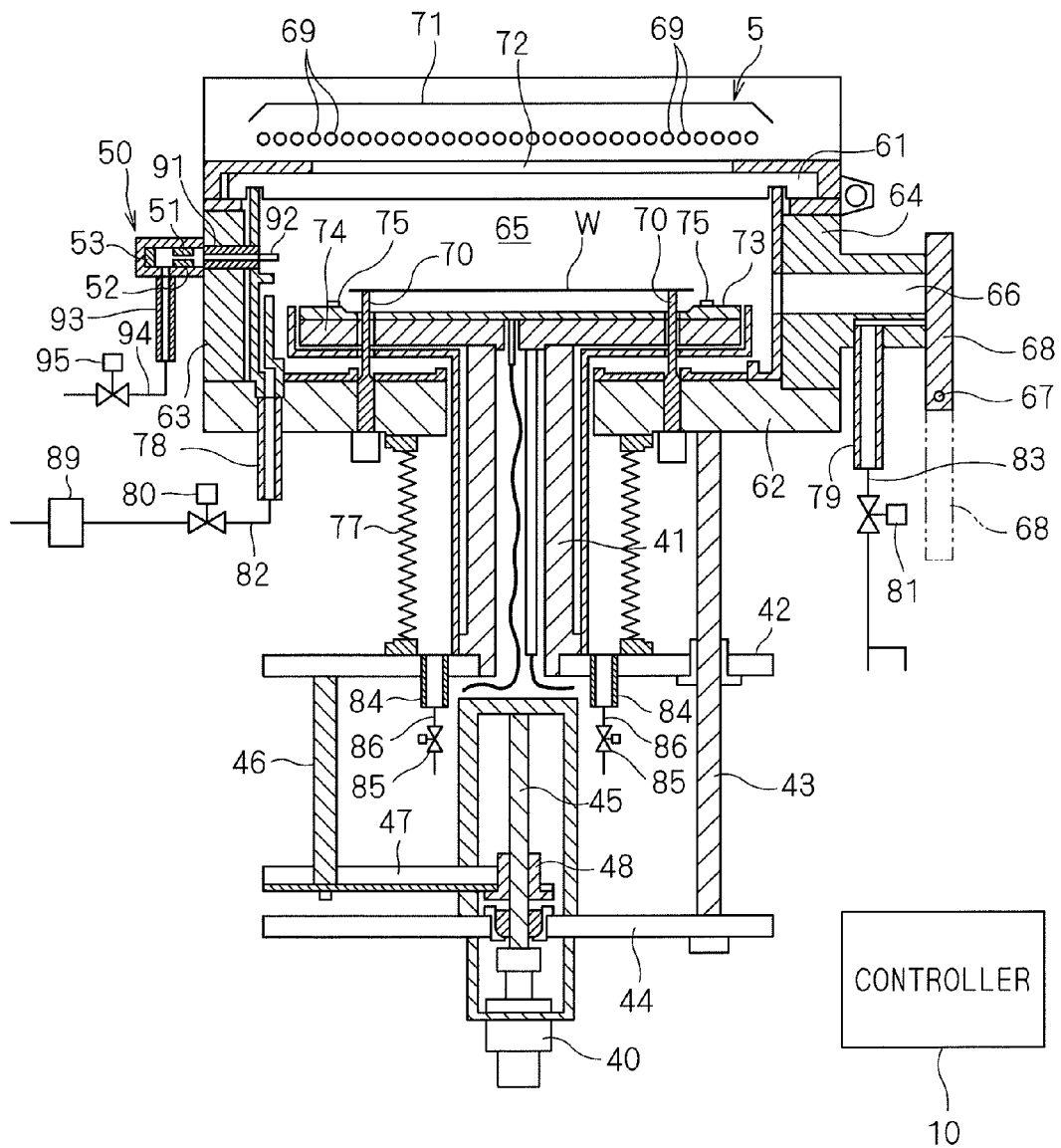
FIG. 1 is a side cross-sectional view showing a configuration of a heat treatment apparatus according to a first preferred embodiment.

Hereinafter, a preferred embodiment of the present invention will be described with reference to the accompanying drawings. Note that the same reference numerals in the drawings denote components that have the same configurations and functions, and a repetitive description thereof will be omitted. Also note that the drawings are merely schematic representations and do not necessarily reflect the exact size, positional relationship, and the like, of the parts shown in the drawings.

First Preferred Embodiment

<1. Configuration of Heat Treatment Apparatus>

Figure 2:
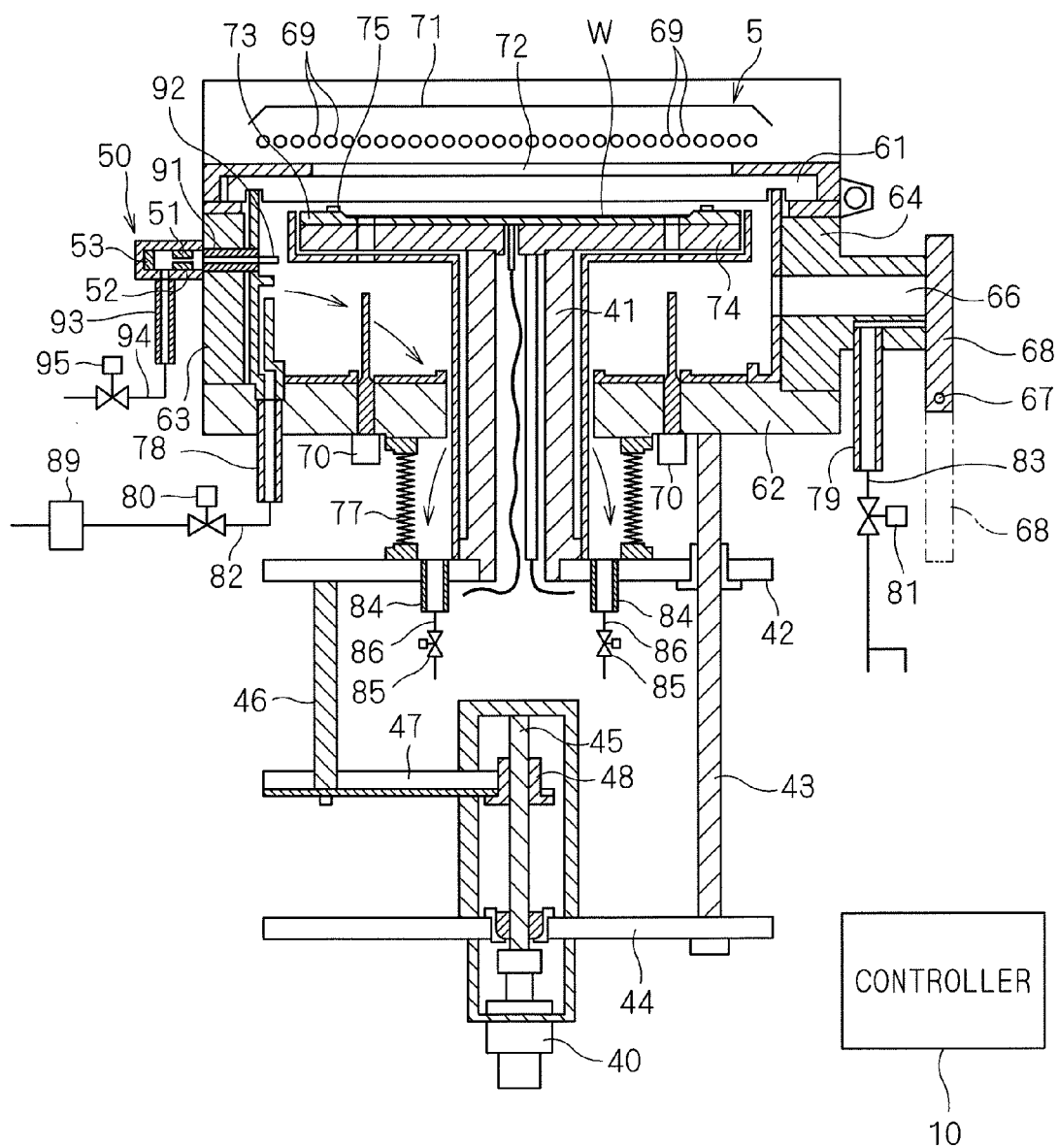
FIG. 2 is a side cross-sectional view showing the configuration of the heat treatment apparatus according to the first preferred embodiment.

FIGS. 1 and 2 are side cross-sectional views showing a configuration of a heat treatment apparatus according to the present invention. The heat treatment apparatus is an apparatus for heat-treating a substrate such as a circular semiconductor wafer by using a light flash (flashes of light) from xenon flash lamps.

The heat treatment apparatus includes a chamber 65. The chamber 65 includes a light-transmittable plate 61, a bottom plate 62, and a pair of side plates 63 and 64, and receives a semiconductor wafer W therein to heat-treat the semiconductor wafer W. The light-transmittable plate 61 constituting an upper portion of the chamber 65 is made of, for example, a material transmissive to infrared light, such as quartz. The light-transmittable plate 61 functions as a chamber window for allowing light emitted from a light source 5 to pass therethrough into the chamber 65. The bottom plate 62 constituting the chamber 65 is provided with upright support pins 70 that extend through a susceptor 73 and a heating plate 74, which will be described later, and support the lower surface of the semiconductor wafer W.

The side plate 64 constituting the chamber 65 is provided with an opening 66 for the transport of the semiconductor wafer W therethrough into and out of the chamber 65. The opening 66 is openable and closable by a gate valve 68 pivoting about an axis 67. With the opening 66 open, the semiconductor wafer W is transported into the chamber 65 by a transport robot (not shown). During a heat treatment of the semiconductor wafer W in the chamber 65, the opening 66 is closed by the gate valve 68.

The chamber 65 is provided under the light source 5. The light source 5 includes a plurality of (in this preferred embodiment, thirty) xenon flash lamps 69 (hereinafter, also referred to simply as "flash lamps 69"), and a reflector 71. The plurality of flash lamps 69, each of which is a rod-like lamp having an elongated cylindrical shape, are arranged in parallel with one another such that a lengthwise direction thereof extends horizontally. The reflector 71 is provided over the plurality of flash lamps 69 to cover all of the flash lamps 69.

Each of the xenon flash lamps 69 includes a glass tube and a trigger electrode. The glass tube contains xenon gas sealed therein, and includes positive and negative electrodes that are provided on opposite ends of the glass tube and that are connected to a capacitor. The trigger electrode is wound around the glass tube. Since the xenon gas is electrically insulative, no current flows in the glass tube in a normal state. However, if a high voltage is applied to the trigger electrode to produce an electrical breakdown, electricity stored in the capacitor flows momentarily in the glass tube, and excitation of xenon atoms or molecules occurring at this time causes light emission. The xenon flash lamps 69 have the property of being capable of emitting much intenser light than a light source that continuously stays lit, because previously stored electrostatic energy is converted into an ultrashort light pulse ranging from 0.1 millisecond to 10 milliseconds.

A light diffusion plate 72 is arranged between the light source 5 and the light-transmittable plate 61. The light diffusion plate 72 used herein is made of quartz glass, which is an infrared-transmissive material, with a surface thereof having been subjected to a light diffusion process.

A part of the light emitted from the flash lamps 69 directly passes through the light diffusion plate 72 and the light-transmittable plate 61 into the chamber 65. A different part of the light emitted from the flash lamps 69 is once reflected from the reflector 71 and then passes through the light diffusion plate 72 and the light-transmittable plate 61 into the chamber 65.

The heating plate 74 and the susceptor 73 are provided in the chamber 65. The susceptor 73 is bonded to the upper surface of the heating plate 74. Pins 75 for preventing the semiconductor wafer W from shifting out of place are mounted on a surface of the susceptor 73. In the chamber 65, the semiconductor wafer W is held in a substantially horizontal attitude directly by the susceptor 73.

The heating plate 74 is provided for preheating (or assist-heating) the semiconductor wafer W. The heating plate 74 is made of aluminum nitride, and is structured to incorporate therein a heater and a sensor for controlling the heater. The susceptor 73, on the other hand, is provided for positioning and holding the semiconductor wafer W and for diffusing thermal energy given from the heating plate 74 to thereby uniformly preheat the semiconductor wafer W. For the susceptor 73, a material having a relatively low thermal conductivity, such as aluminum nitride or quartz, is adopted.

The susceptor 73 and the heating plate 74 are driven by a motor 40 to vertically move between a wafer transport position in which the semiconductor wafer W is transported into and out of the chamber 65 as shown in FIG. 1 and a wafer heat treatment position in which the semiconductor wafer W is heat-treated as shown in FIG. 2.

Specifically, the heating plate 74 is coupled to a movable plate 42 by a tubular element 41. The movable plate 42 is guided by a guide member 43 suspended from the bottom plate 62 of the chamber 65 such that the movable plate 42 is vertically movable. A fixed plate 44 is fixed to the lower end of the guide member 43, and the motor 40 for rotatably driving a ball screw 45 is provided in a central portion of the fixed plate 44. The ball screw 45 is in threaded engagement with a nut 48 coupled to the movable plate 42 by coupling members 46 and 47. With this arrangement, the susceptor 73 and the heating plate 74 are driven by the motor 40 and thereby can be moved vertically between the wafer transport position in which the semiconductor wafer W is transported into and out of the chamber 65 as shown in FIG. 1 and the wafer heat treatment position in which the semiconductor wafer W is heat-treated as shown in FIG. 2.

The wafer transport position shown in FIG. 1 corresponds to the position of the susceptor 73 and the heating plate 74 being lowered so that the semiconductor wafer W transported through the opening 66 into the chamber 65 is placed onto the support pins 70 by means of the transport robot (not shown) or so that the semiconductor wafer W placed on the support pins 70 is transported through the opening 66 out of the chamber 65 by means of the transport robot (not shown). Specifically, the susceptor 73 and the heating plate 74 which are vertically movable are provided with through holes which enable the support pins 70 fixed upright on the bottom plate 62 to pass therethrough relative to the susceptor 73 and the heating plate 74. When the susceptor 73 and the heating plate 74 move downward to the wafer transport position, the upper ends of the support pins 70 protrude out of the upper surface of the susceptor 73 and a state where the semiconductor wafer W is receivable thereon is created, as shown in FIG. 1.

The wafer heat treatment position shown in FIG. 2, on the other hand, corresponds to the position of the susceptor 73 and the heating plate 74 being raised above the upper ends of the support pins 70 for the heat treatment of the semiconductor wafer W. When the susceptor 73 and the heating plate 74 move upward to the wafer heat treatment position, the upper ends of the support pins 70 are below the upper surface of the susceptor 73 as shown in FIG. 2, and the semiconductor wafer W placed on the support pins 70 is received by the susceptor 73. Thus, the motor 40 vertically moves the susceptor 73 and the heating plate 74 relative to the support pins 70 between the wafer transport position shown in FIG. 1 and the wafer heat treatment position shown in FIG. 2.

In the course of the downward movement of the susceptor 73 and the heating plate 74 from the wafer heat treatment position shown in FIG. 2 to the wafer transport position shown in FIG. 1, the semiconductor wafer W supported by the susceptor 73 is transferred to the support pins 70. On the other hand, in the course of the upward movement of the susceptor 73 and the heating plate 74 from the wafer transport position shown in FIG. 1 to the wafer heat treatment position shown in FIG. 2, the semiconductor wafer W placed on the support pins 70 is received by the susceptor 73, is lifted with the lower surface thereof supported by the upper surface of the susceptor 73, and is held in a horizontal attitude in proximity to the light-transmittable plate 61 in the chamber 65.

When the susceptor 73 and the heating plate 74 that support the semiconductor wafer W are raised to the wafer heat treatment position, the light-transmittable plate 61 is situated between the light source 5 and the semiconductor wafer W held by the susceptor 73 and heating plate 74. A distance between the susceptor 73 and the light source 5 at this time is adjustable to any value by controlling the amount of rotation of the motor 40.

An expandable/contractible bellows 77 surrounding the tubular element 41 for maintaining the chamber 65 hermetically sealed is provided between the bottom plate 62 of the chamber 65 and the movable plate 42. The bellows 77 contacts when the susceptor 73 and the heating plate 74 are raised to the wafer heat treatment position, and expands when the susceptor 73 and the heating plate 74 are lowered to the wafer transport position. The bellows 77 cuts off communication between an atmosphere inside the chamber 65 and the external atmosphere.

The side plate 63 of the chamber 65 arranged on the side opposite to the opening 66 is formed with an inlet passage 78. The inlet passage 78 is connected in communication with a gas source (not shown) through a gas pipe 82. An open-close valve 80 and a mass flow controller 89 are provided in the gas pipe 82. Opening the open-close valve 80 can supply a gas that is required for a process, such as an inert nitrogen gas, into the chamber 65 through the distal end of the inlet passage 78. The flow rate of the nitrogen gas supplied into the chamber 65 is controlled by the mass flow controller 89. At this time, the nitrogen gas is ejected in a substantially horizontal direction. When the nitrogen gas is supplied through the inlet passage 78 while the susceptor 73 and the heating plate 74 are raised to the wafer heat treatment position, the nitrogen gas is supplied to a space between the heating plate 74 and the bottom plate 62, as shown in FIG. 2. In other words, the inert nitrogen gas is supplied to a bottom portion of the chamber 65.

The opening 66 in the side plate 64, on the other hand, is provided with an outlet passage 79. The outlet passage 79 is connected in communication with an exhaust element (not shown) through an exhaust pipe 83. An open-close valve 81 is provided in the exhaust pipe 83. Opening the open-close valve 81 causes the gas existing in the chamber 65 to be discharged out of the outlet passage 79 through the opening 66. The exhaust pipe 83 is branched into to pipes, namely, a large-diameter pipe and a small-diameter pipe, and switching therebetween is implemented by a switching valve (not shown). To exhaust the chamber 65 with a high flow rate, the large-diameter pipe is selected. To exhaust the chamber 65 with a low flow rate, the small-diameter pipe is selected.

The movable plate 42 is also formed with outlet passages 84. The distal ends of the respective outlet passages 84 are in communication with the space between the bellows 77 and the tubular element 41, and the proximal ends thereof are connected in communication with an exhaust element (not shown) via exhaust pipes 86, respectively. Open-close valves 85 are provided in the exhaust pipes 86, respectively. Opening the open-close valves 85 causes the gas existing in the chamber 65 to be discharged out of the outlet passages 84 through the space between the bellows 77 and the tubular element 41. In other words, the outlet passages 84 exhaust the gas in the interior space of the chamber 65 through the bottom portion of the chamber 65, as shown in FIG. 2.

The side plate 63 is also formed with an inlet passage 91 extending through the side plate 63. A tubular probe 92 having an inlet passage therein is provided at the end of the inlet passage 91 on the chamber 65 side, and a measurement part 50 is provided at the opposite end of the inlet passage 91. In the measurement part 50, a measurement chamber having a light emitting part 51, a light receiving part 52, and the like, is formed. Via the inlet passage 91 and the probe 92, a measurement space within the measurement chamber is connected in communication with a processing space within the chamber 65. The measurement chamber of the measurement part 50 is formed with an outlet passage 93, and connected in communication with an exhaust system (not shown) via an exhaust pipe 94. The inside diameter of the outlet passage 93 that exhausts the measurement part 50 is smaller than the inside diameters of the outlet passages 79 and 84 that exhaust the inside of the chamber 65. An open-close valve 95 is provided in the exhaust pipe 94. Opening the open-close valve 95 causes the gas existing in the processing space of the chamber 65, to which pressure has been applied due to the introduction of the nitrogen gas and the like, to be introduced into the measurement chamber of the measurement part 50 with a substantially constant flow rate. The measurement space of the measurement part 50 is tightly sealed by a portion of the side plate 63 defining the edge of the opening of the inlet passage 91, in order to prevent a gas from entering the measurement chamber from places other than the processing space of the chamber 65. The probe 92 is provided for the purpose of introducing, into the measurement part 50, a gas existing in a place closer to an objective substrate to be processed. However, the usefulness of the present invention is not impaired even though a gas existing in any place in the processing space within the chamber 65 is introduced into the measurement chamber of the measurement part 50. Therefore, the probe 92 is not an essential element.

The measurement part 50 is configured as an optical particle counter (OPC), to measure a particle concentration ("air particle concentration") in a gas existing within the chamber 65 which has been introduced into the measurement chamber of the measurement part 50. The measurement part 50 mainly includes the light emitting part 51, the light receiving part 52, and a control computation part 53. The light emitting part 51 is provided with a laser light source such as a semiconductor laser (not shown), a light-emitting optical system, and the like. The light receiving part 52 is provided with a light-receiving optical system (not shown), a processing circuit including a detection device such as a photodiode, and the like. Laser light emitted from the laser light source is condensed by the light-emitting optical system, and then emitted to a passage formed between the light emitting part 51 and the light receiving part 52. In this passage, a gas introduced from the processing space within the chamber 65 into the measurement chamber of the measurement part 50 flows. When the laser light hits a particle contained in the gas, scattering light is generated. The scattering light is, by the light-receiving optical system, imaged onto the detection device of the processing circuit. Then, the processing circuit outputs an electric pulse signal corresponding to each scattering light that has been incident on the detection device. The electric pulse signal is supplied to the control computation part 53.

The control computation part 53 is implemented by, for example, execution of a predetermined program by a CPU. The control computation part 53 controls operations of the light emitting part 51 and the light receiving part 52, and processes the pulse signal supplied from the processing circuit of the light receiving part 52. The crest value of this pulse signal is proportional to the amount of scattering light. A correlation based on the scattering theory is established between the amount of scattering light and a particle diameter of the particle. The particle diameter is calculated based on the crest value of the pulse signal. The control computation part 53 calculates the particle diameter of the particle with respect to each of the electric pulse signals supplied from the light receiving part 52, and, based on a predetermined size (particle diameter) that is preliminarily stored in a memory of the control computation part 53, determines whether the calculated particle diameter is less than or not less than the predetermined size.

Based on a result of the determination, the control computation part 53 counts the number of particles having particle diameters not less than the predetermined size which have been measured within a certain time period, and the number of particles having particle diameters less than the predetermined size which have been counted within the certain time period. Then, the control computation part 53 calculates a particle concentration of the particles having particle diameters not less than the predetermined size and a particle concentration of the particles having particle diameters less than the predetermined size, based on the flow rate of a gas that passes per unit time through the passage between the light emitting part 51 and the light receiving part 52, which is preliminarily stored in the memory. Thereby, the control computation part 53 measures two kinds of particle concentrations. Here, it may be also possible that the control computation part 53 measures only one of the two kinds of particle concentrations in accordance with a control given by the controller 10. The particle concentrations measured by the control computation part 53 are supplied to the controller 10, and used by the controller 10 for the conversion into the number of particles existing on the substrate, the determination of whether or not the particle concentration is at a predetermined level, and the like.

In a case where the measurement part 50 is provided inside the outlet passage 79 or 84 that exhausts the interior of the chamber 65, there is a possibility that a particle concentration obtained as a result of the measurement is higher than the actual particle concentration in the chamber 65, because of an influence of various remaining particles such as metal particles that have been attached to the inside of the outlet passage at a time of processing the outlet passage 79 or 84. In this respect, the heat treatment apparatus according to this preferred embodiment has the outlet passage 93 that is dedicated for exhaust of the measurement part 50, so that the air particle concentration in the gas that has been introduced into the measurement chamber of the measurement part 50 by the exhaust using the outlet passage 93 is measured. This can suppress a measurement error in measuring the particle concentration, which may be normally caused because of contamination of the inside of the outlet passage 79 or 84.

The above-mentioned heat treatment apparatus further includes a controller 10 for controlling mechanical components such as the motor 40. FIG. 3 is a block diagram showing a configuration of the controller 10. The controller 10 is similar to a typical computer in terms of a hardware configuration. Specifically, the controller 10 includes a CPU 11 for performing various computation processes, a ROM 12 or read-only memory for storing a basic program therein, a RAM 13 or readable/writable memory for storing various pieces of information, a magnetic disk 14 for storing control software and data therein, and a bus line 19 connected to these components 11 to 14.

The bus line 19 is electrically connected to a display part 21 and an input part 22. The display part 21 is configured with, for example, a liquid crystal display, and displays various pieces of information such as processing results and recipe details. The input part 22 is configured with, for example, a keyboard and a mouse, and accepts the entry of a command, a parameter, and the like. An operator of the heat treatment apparatus can enter a command, a parameter, and the like, through the input part 22 while viewing the descriptions displayed on the display part 21. The display part 21 and the input part 22 may be integrated together into a touch panel device.

The bus line 19 is also electrically connected to the motor 40 of the heat treatment apparatus, the measurement part 50, a lamp power supply circuit (not shown) for the flash lamps 69, and the open-close valves 80, 81, 85, and 95. The bus line 19 is furthermore connected to the switching valve of the exhaust pipe 83 and the mass flow controller 89 of the gas pipe 82. The CPU 11 of the controller 10 executes predetermined software stored in the magnetic disk 14, and thereby controls the turn-on timing of the flash lamps 69 and also controls the motor 40 to adjust the vertical position of the susceptor 73 and the heating plate 74. Additionally, the CPU 11 controls the open-close valves, to thereby control the supply and exhaust of gases to and out of the chamber 65 and the measurement chamber of the measurement part 50. Moreover, the CPU 11 controls an operation of the measurement part 50, and, based on the particle concentration supplied from the measurement part 50, calculates the number of particles attached to the substrate received in the chamber 65.

Figure 4:
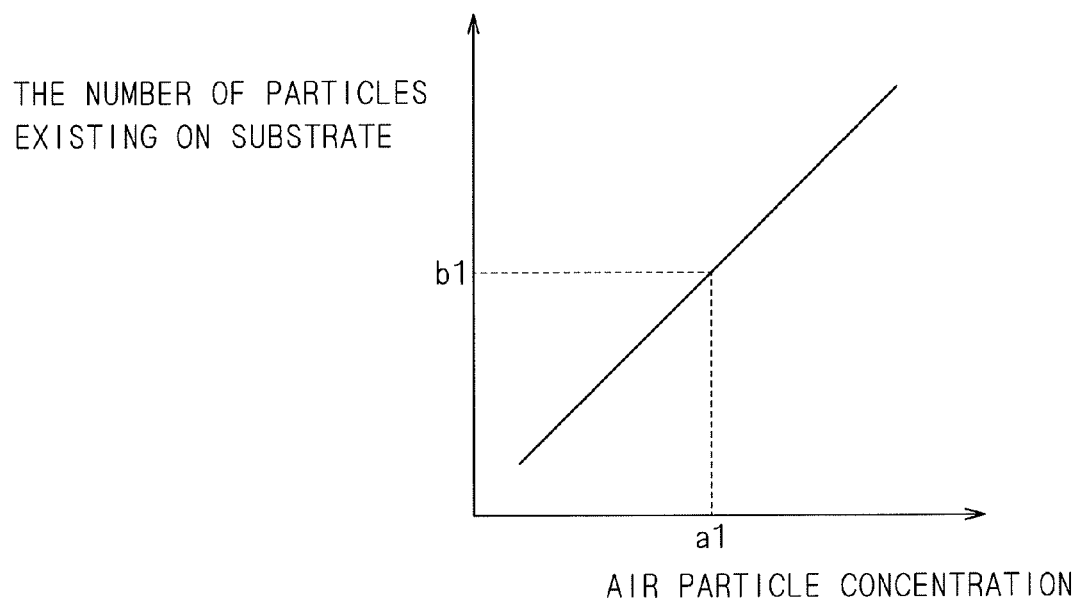
FIG. 4 shows an example of the correlation between an air particle concentration and the number of particles existing on a substrate.

FIG. 4 shows an example of the correlation between the air particle concentration and the number of particles existing on the substrate received in the chamber 65. As shown in FIG. 4, there is a correlation between the air particle concentration in the processing space of the chamber 65 and the number of particles attached to the substrate received in the chamber 65. Normally, the number of particles existing on the substrate is proportional to the air particle concentration. Such a correlation can be obtained in advance by means of experiments and simulations. Correlation information indicating the correlation is preliminarily identified and stored in the magnetic disk 14. Examples of the correlation information include a table indicating the correlation, a mathematical expression, and various other types of information. Based on the correlation information and an air particle concentrational measured by the measurement part 50, the CPU 11 calculates the number b1 of particles that will be attached to the substrate intended to be received in the chamber 65. Instead, based on the correlation information, the CPU 11 can calculate an air particle concentrational corresponding to a target number b1 of particles existing on the substrate. Furthermore, the CPU 11 also determines whether or not the air particle concentration obtained as a result of the measurement is equal to or less than a predetermined reference value stored in the magnetic disk 14. It may be also possible that the CPU 11 performs a determination corresponding to this determination, by converting the air particle concentration into the number of particles existing on the substrate.

The magnetic disk 14 stores not only the above-described correlation information but also various pieces of information used for an apparatus start-up process that follows the maintenance. The various pieces of information include the number of times and a time interval of emission of flashes of light during the cleaning process, the predetermined size (particle diameter) serving as a criterion for determining the size of the particle diameter, a reference concentration for the particle concentration, and the like. The above-mentioned predetermined size of the particle is supplied to, for example, the memory of the control computation part 53 of the measurement part 50, and used by the measurement part 50.

<2. Details of Process in Heat Treatment Apparatus>

Figure 5:
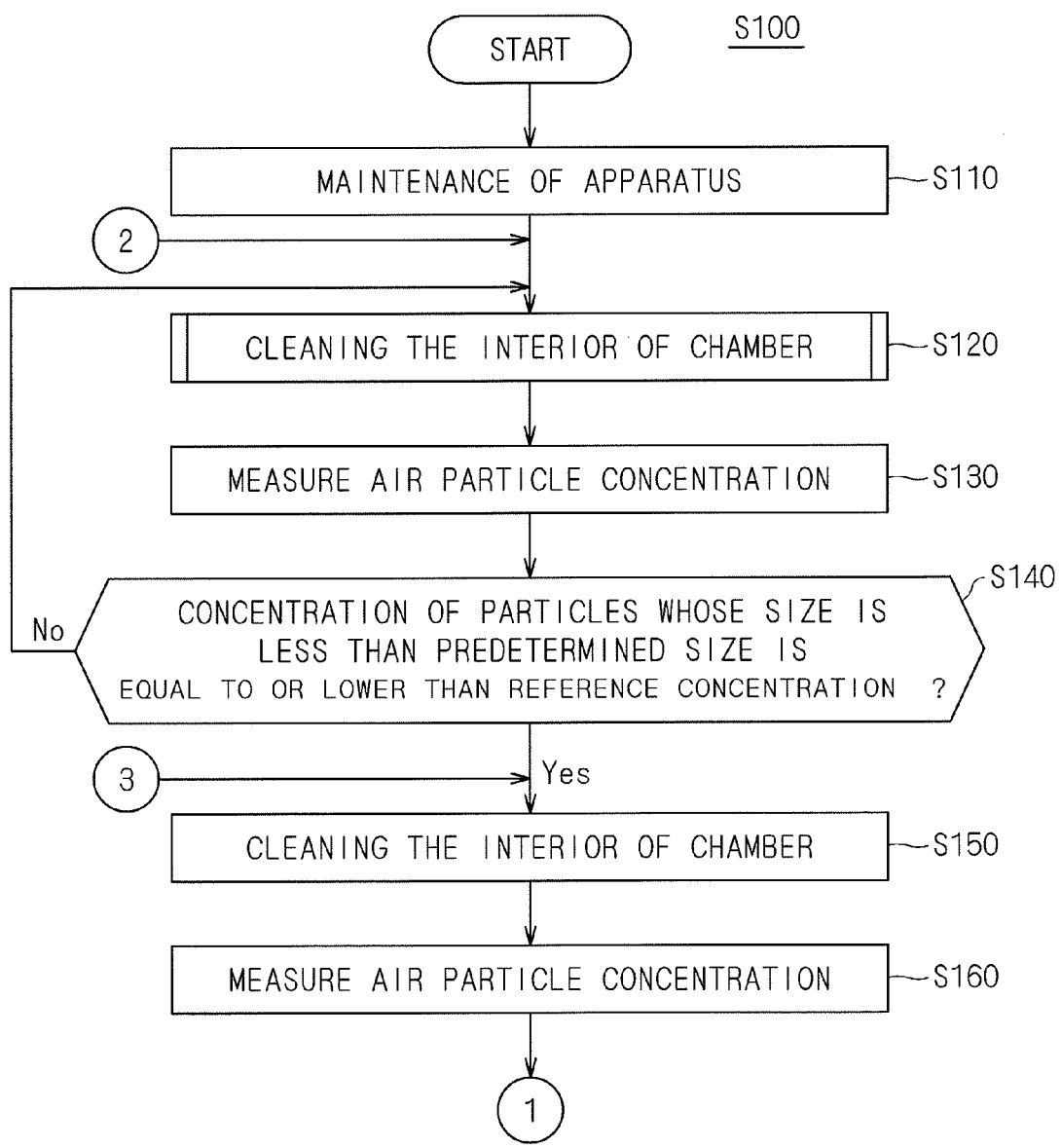
FIG. 5 is a flowchart of a process in the heat treatment apparatus according to the first preferred embodiment.
Figure 6:
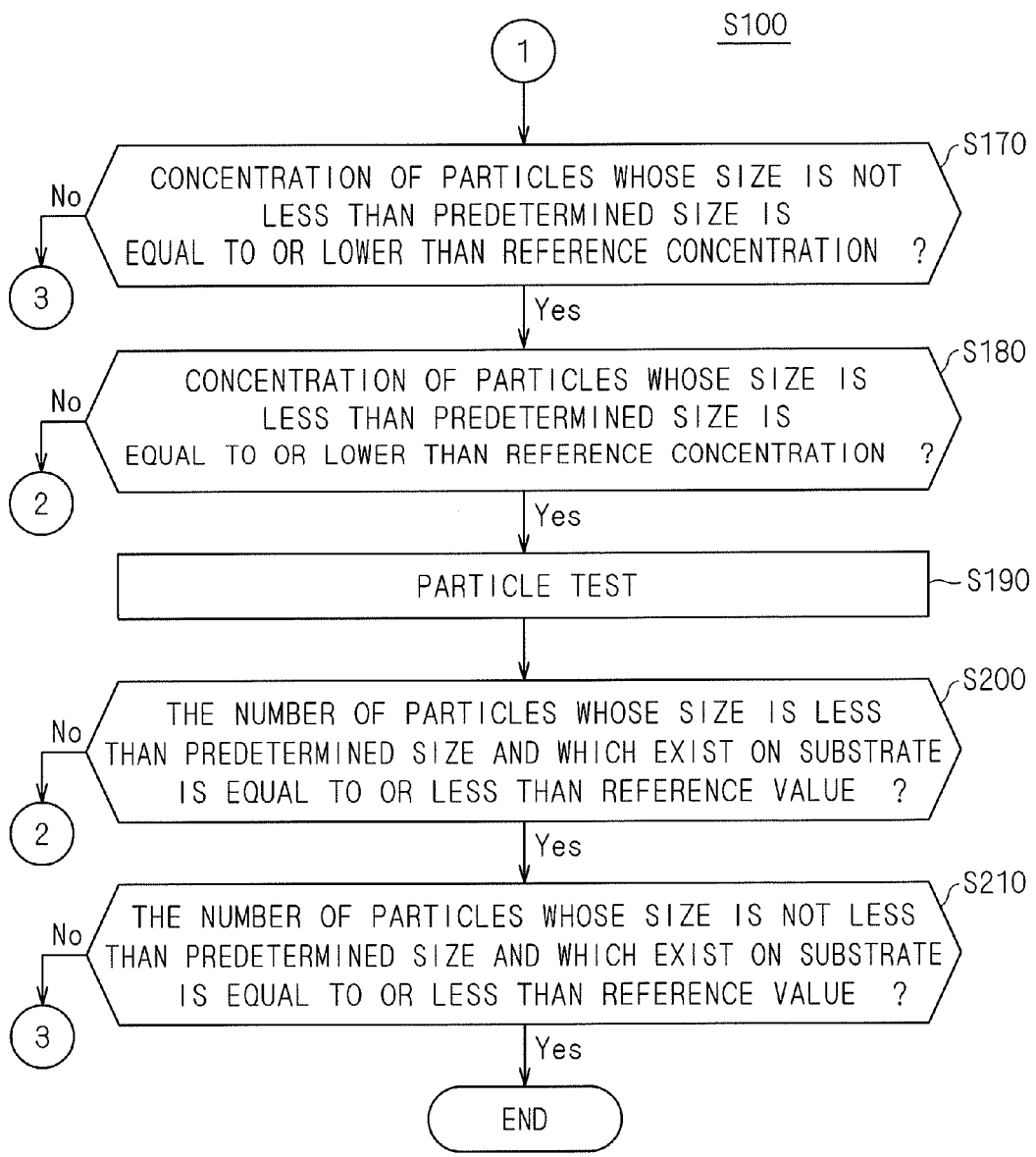
FIG. 6 is a flowchart of the process in the heat treatment apparatus according to the first preferred embodiment.
Figure 7:
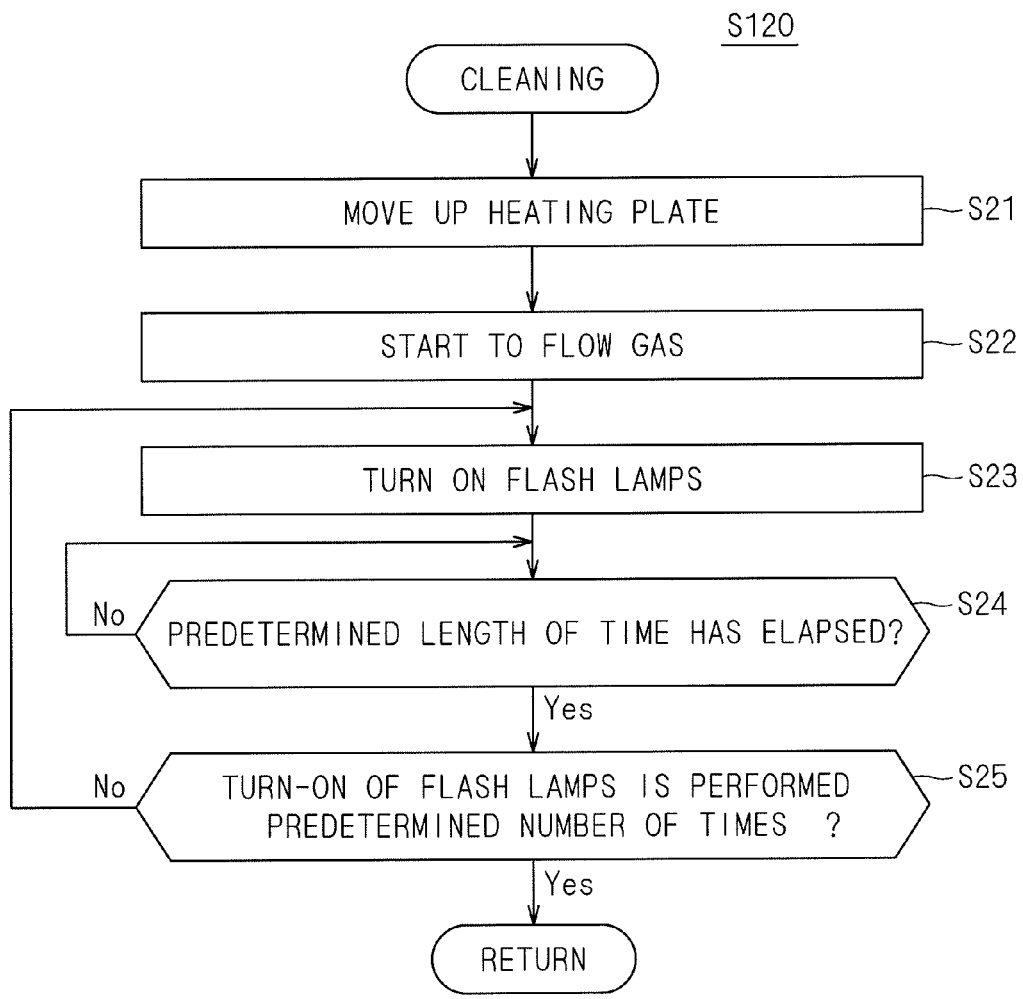
FIG. 7 is a flowchart of a process in the heat treatment apparatus according to the first preferred embodiment.

Next, a process in the heat treatment apparatus according to the present invention will be described. FIGS. 5 to 7 are flowcharts showing a process in the heat treatment apparatus according to the present invention. FIGS. 5 and 6 show a process flow S100 of the apparatus start-up process in a case where the maintenance is carried out in the heat treatment apparatus. FIG. 7 shows details of step S120 (FIG. 5) concerning the cleaning process (cleaning process) for cleaning the interior of the chamber 65. The cleaning process shown in FIG. 7 is performed by actuation of the mechanical components including the lamp power supply circuit in accordance with instructions given from the controller 10.

First, the maintenance of the heat treatment apparatus is carried out in step S110. The maintenance in step S110 may be carried out at regular time intervals or at irregular time intervals, for example, whenever a breakage of the semiconductor wafer W occurs in the chamber 65. In either case, the maintenance is carried out while the light source 5 is removed and the interior of the chamber 65 is open to the external atmosphere. This causes external particles to enter the chamber 65 during the maintenance. If the maintenance is due to a breakage of the semiconductor wafer W, additional particles are generated from broken pieces of the semiconductor wafer W.

After a predetermined maintenance process, the process proceeds to step S120. In step S120, the light source 5 is mounted to the upper portion of the chamber 65 (to create the state shown in FIG. 1), and the cleaning process is performed to clean the interior of the chamber 65. In the cleaning process, the transport robot that transports a substrate into the chamber 65 and the gate valve 68 are not driven. Then, particles existing in the chamber 65 and having particle diameters less than the predetermined size (particle diameter), for example, having particle diameters less than 0.8 um, are removed.

For performing the cleaning process, firstly, any objective semiconductor wafer W to be processed is prohibited from being transported into the chamber 65, and the susceptor 73 and the heating plate 74 are moved upward to the wafer heat treatment position shown in FIG. 2 (in step S21). Thus, during the cleaning process, there is no semiconductor wafer W in the chamber 65, and the susceptor 73 with no semiconductor wafer W placed thereon is moved upward to the wafer heat treatment position. The heater in the heating plate 74 is turned ON to start heating the heating plate 74.

After the susceptor 73 and the heating plate 74 move upward to the wafer heat treatment position, a stream of nitrogen gas is produced in the chamber 65 (in step S22). Specifically, the open-close valves 80, 81 and 85 are opened, to thereby produce a stream of nitrogen gas directed from the inlet passage 78 toward the outlet passages 79 and 84. Although the open-close valve 81 may remain closed, the open-close valves 85 must be opened without fail. This produces a gas stream passing through a bottom portion of the chamber 65 and then exhausted out of the chamber 65, as indicated by the arrows in FIG. 2.

From the viewpoint of accurately determining whether or not there is a necessity to perform the cleaning again at a time when the cleaning process for cleaning the interior of the chamber 65 is completed, it is preferable that a gas obtained at a time when the cleaning is completed so that the particle concentration in the processing space of the chamber 65 is made substantially uniform is introduced into the measurement chamber of the measurement part 50. In a case where the open-close valve 95 is opened, there is a risk that, when the turn-on of the flash lamps 69 is started, the particles may fly up from the bottom portion of the chamber 65 and the like, so that a gas having a locally high particle concentration is introduced into the measurement part 50, which results in an inaccurate particle concentration being measured. Therefore, although the usefulness of the present invention is not impaired even when the open-close valve 95 is not provided in the exhaust pipe 94, it is more preferable to provide the exhaust pipe 94 and close the open-close valve 95 before the turn-on of the flash lamps 69 is started.

Thereafter, the flash lamps 69 are turned on to emit flashes of light toward the interior of the chamber 65 (in step S23). A length of time during which the flash lamps 69 are ON ranges from about 0.1 millisecond to about 10 milliseconds. The flash lamps 69 emit extremely intense flashes of light toward the interior of the chamber 65 because previously stored electrostatic energy is converted into such an ultra-short light pulse. The emission of the flashes of light from the flash lamps 69 heats the gas and the structural components in the chamber 65 so that instantaneous expansion and contraction of the gas in the chamber 65 occurs, resulting in particles being raised and scattering in the chamber 65. Particularly in the bottom portion (the upper surface of the bottom plate 62) of the chamber 65, the particles are likely to be deposited. However, as illustrated in this preferred embodiment, emitting the flashes of light under the state where the heating plate 74 is moved up to the wafer heat treatment position can easily cause such particles deposited on the bottom portion to be raised up.

The particles scattering in this manner is carried by the stream of nitrogen gas and discharged to the outside of the chamber 65. As described above, the particles are likely to scatter particularly near the bottom portion of the chamber 65. However, in this preferred embodiment, the gas stream passing through the bottom portion of the chamber 65 and then exhausted out of the chamber 65 is produced. Therefore, the particles scattering near the bottom portion of the chamber 65 is efficiently discharged to the outside of the chamber 65.

The controller 10 determines whether or not a predetermined length of time has elapsed since the turn-on of the flash lamps 69 (in step S24). That is, after the emission of the flashes of light is performed once, discharging of the particles is performed for the predetermined length of time. The stream of nitrogen gas passing through the bottom portion of the chamber 65 and then exhausted out of the chamber 65 continues to be produced even during the lapse of the predetermined length of time. As the predetermined length of time, for example, one minute is set.

After the predetermined length of time has elapsed, a considerable amount of particles is discharged to the outside of the chamber 65, but some particles are deposited again on the bottom portion of the chamber 65. Then, the controller 10 determines whether or not the turn-on of the flash lamps 69 has been performed a predetermined number of times (in step S25). For example, 50 times to 100 times is adopted as the predetermined number of times. When the number of times the turn-on of the flash lamps 69 is performed is less than the predetermined number of times, the process returns to step S23 in which the flash lamps 69 are turned on again. The emission of flashes of light by the turn-on of the flash lamps 69 causes the particles deposited again to rise and scatter, and the stream of nitrogen gas carries the particles to the outside of the chamber 65. When the number of times the turn-on of the flash lamps 69 is performed has reached the predetermined number of times, the cleaning process is terminated.

Referring to FIG. 5 again, after the cleaning process for cleaning the interior of the chamber 65 is completed, the process proceeds to step S130 in which an air particle concentration is measured. Prior to the measurement of the air particle concentration, the open-close valve 95 is opened so that the gas existing in the chamber 65 is introduced into the measurement chamber of the measurement part 50. Then, the measurement part 50 measures, from a particle concentration of particles having particle diameters not less than the predetermined size (particle diameter) and a particle concentration of particles having particle diameters less than the predetermined size (particle diameter), at least the particle concentration of particles having particle diameters less than the predetermined size. Then, the measurement part 50 supplies a result of the measurement to the controller 10.

Then, in step S140, the controller 10 determines whether or not the particle concentration of particles having particle diameters less than the predetermined size is equal to or lower than a predetermined reference value. When, as a result of the determination, the particle concentration is higher than the reference value, the process returns to step S120, in which the cleaning of the interior of the chamber 65 is performed again. When, as a result of the determination, the particle concentration is equal to or lower than the reference value, the process proceeds to step S150, in which cleaning of the interior of the chamber 65 is newly performed. This new cleaning process is performed under a state where a transport operation of the transport robot, an open/close operation of the gate valve 68 are performed as if a substrate was transported into the chamber 65. During the process, the turn-on of the flash lamps 69 is, for example, repeated 25 times to 50 times at intervals of one minute. Except for these different points, the cleaning process performed in step S150 is the same as the process performed in step S120. As a result of this cleaning process, particles existing in the chamber 65 and having particle diameters not less than the predetermined size (particle diameter), for example, having particle diameters not less than 0.8 um, are mainly removed. That is, in the process of step S150, particles having particle diameters larger than the particle diameters of the particles mainly removed in the cleaning of step S120 are mainly removed.

After the cleaning process for cleaning the interior of the chamber 65 is completed in step S150, the process proceeds to step S160, in which the open-close valve 95 is opened so that an air particle concentration is measured in the same manner as in the measurement in step S130. However, in the measurement in step S160, the measurement part 50 measures both of a particle concentration of particles having particle diameters not less than the predetermined size (particle diameter) and a particle concentration of particles having particle diameters less than the predetermined size (particle diameter). Then, the measurement part 50 supplies a result of the measurement to the controller 10.

Then, in step S170 of FIG. 6, the controller 10 determines whether or not the supplied particle concentration of particles having particle diameters not less than the predetermined size is equal to or lower than a predetermined reference value. When, as a result of the determination, the particle concentration is higher than the reference value, the process returns to step S150, in which the cleaning of the interior of the chamber 65 is performed again. When, as a result of the determination, the particle concentration is equal to or lower than the reference value, the process proceeds to step S180, in which the controller 10 determines whether or not the particle concentration of particles having particle diameters less than the predetermined size is equal to or lower than the reference value. When, as a result of the determination, the particle concentration is higher than the reference value, the process returns to step S120, in which the cleaning of the interior of the chamber 65 is performed again. When, as a result of the determination, the particle concentration is equal to or lower than the reference value, a particle test of step S190 is conducted. In the particle test, as already described, a dummy wafer is actually received in the chamber 65 and subjected to the same heat treatment as the heat treatment performed on the objective semiconductor wafer W to be processed. Then, the dummy wafer is taken out of the chamber 65, and then transported into a measurement machine that is separately provided. Thereby, the number of particles attached onto the substrate is actually measured. This measurement is performed for both of particles having particle diameters not less than the predetermined size, for example, not less than 0.8 um, and particles having particle diameters less than the predetermined size.

After the number of particles existing on the substrate is measured, then in step S200, whether or not the number of particles having particle diameters less than the predetermined size is equal to or smaller than a reference value is determined. The reference value is, for example, ten. When, as a result of the determination, the number of the particles larger than the reference value, the process returns to step S120, in which the cleaning of the interior of the chamber 65 is performed again. When, as a result of the determination, the number of the particle is not larger than the reference value, the determination of step S210 is made to determine whether or not the number of particles having particle diameters not less than the predetermined size is equal to or smaller than a reference value. The reference value is, for example, twenty. When, as a result of the determination, the number of the particles is larger than the reference value, the process returns to step S150, in which the cleaning of the interior of the chamber 65 is performed again. When, as a result of the determination, the number of the particles is equal to or smaller than the reference value, the start-up process that follows the maintenance of the heat treatment apparatus is terminated.

After the start-up process that follows the maintenance of the heat treatment apparatus is completed, the semiconductor wafer W is heat-treated. An objective semiconductor wafer W to be heat-treated in the heat treatment apparatus is a semiconductor wafer implanted with ions.

In a heat treatment step, with the susceptor 73 and the heating plate 74 situated in the wafer transport position shown in FIG. 1, the transport robot (not shown) transports the semiconductor wafer W through the opening 66 into the chamber 65, and places the semiconductor wafer W onto the support pins 70. After the semiconductor wafer W is received in the chamber 65, the opening 66 is closed by the gate valve 68. Thereafter, the susceptor 73 and the heating plate 74 are driven by the motor 40 to move upward to the wafer heat treatment position shown in FIG. 2, thereby holding the semiconductor wafer W in a horizontal attitude. The open-close valves 80, 81 and 85 are opened to produce the stream of nitrogen gas in the chamber 65.

The susceptor 73 and the heating plate 74 are heated in advance to a predetermined temperature under the action of the heater incorporated in the heating plate 74. Thus, in a state where the susceptor 73 and the heating plate 74 are moved upward to the wafer heat treatment position, the semiconductor wafer W is preheated by contacting the susceptor 73 that is heated. Thus, the temperature of the semiconductor wafer W rises gradually.

In this state, the semiconductor wafer W is heated through the susceptor 73 without interruption. During the temperature rise of the semiconductor wafer W, a temperature sensor (not shown) always monitors whether or not the surface temperature of the semiconductor wafer W has reached a preheating temperature T1.

The preheating temperature T1 ranges, for example, from about 200° C. to about 600° C. Heating the semiconductor wafer W to the preheating temperature T1 within such a range does not diffuse the ions implanted in the semiconductor wafer W.

When the surface temperature of the semiconductor wafer W reaches the preheating temperature T1, the flash lamps 69 are turned on to perform flash heating. A length of time during which the flash lamps 69 are ON in the flash heating step ranges from about 0.1 millisecond to about 10 milliseconds. The flash lamps 69 emit extremely intense flashes of light because previously stored electrostatic energy is converted into such an ultrashort light pulse.

Such flash heating causes the surface temperature of the semiconductor wafer W to instantaneously reach a temperature T2. The temperature T2 is a temperature ranging from about 1000° C. to about 1100° C. and required for a process of activating the ions in the semiconductor wafer W. The temperature rise of the surface of the semiconductor wafer W to this treatment temperature T2 activates the ions implanted in the semiconductor wafer W.

In this process, the activation of the ions in the semiconductor wafer W is completed in a short time because the surface temperature of the semiconductor wafer W is raised to the treatment temperature T2 in an extremely short time ranging from about 0.1 millisecond to 10 milliseconds. This causes no diffusion of the ions implanted in the semiconductor wafer W, and therefore can prevent occurrence of a phenomenon in which the ions implanted in the semiconductor wafer W exhibit a round or dull profile. Because a length of time required for the activation of ions is much shorter than a length of time required for the diffusion of the ions, the activation of the ions is completed even in a short time ranging from about 0.1 millisecond to about 10 milliseconds which causes no diffusion.

Additionally, before the flash lamps 69 are turned on to heat the semiconductor wafer W, the surface temperature of the semiconductor wafer W is raised up to the preheating temperature T1 ranging from about 200° C. to about 600° C. by using of the heating plate 74. This enables the temperature of the semiconductor wafer W to be rapidly raised up to the treatment temperature T2 ranging from about 1000° C. to about 1100° C. by the flash lamps 69.

After the flash heating step, the susceptor 73 and the heating plate 74 are driven by the motor 40 to move downward to the wafer transport position shown in FIG. 1, and the opening 66 having been closed by the gate valve 68 is opened. The transport robot (not shown) transports the semiconductor wafer W placed on the support pins 70 out of the chamber 65. In the above-mentioned manner, a series of heat treatment operations is completed.

In the heat treatment apparatus according to this preferred embodiment having the above-described configuration, the air particle concentration in the processing space of the chamber 65 is measured by the measurement part 50. The air particle concentration is correlated with the number of particles attached to the substrate that is received in the process chamber. Therefore, by conducting the particle test after the air particle concentration in the processing space is lowered to an air particle concentration corresponding to the number of particles existing on a substrate which can pass the particle test, the number of times the particle test should be conducted after the maintenance of the heat treatment apparatus can be reduced. Additionally, since the measurement part 50 is provided in the apparatus itself, time and effort required for measurement of the air particle concentration are much smaller than those required for the particle test. Accordingly, the heat treatment apparatus according to this preferred embodiment can achieve a considerable cost reduction.

Moreover, in the heat treatment apparatus according to this preferred embodiment having the above-described configuration, the correlation information indicating the correlation between the air particle concentration in the processing space of the chamber 65 and the number of particles attached to the substrate received in the chamber 65 is stored in the magnetic disk 14. Based on a result of the measurement by the measurement part 50 and the correlation information, the controller 10 calculates the number of particles that will be attached to a substrate intended to be received in the chamber 65. The particle test is conducted only when the particle concentration in the processing space is equal to or lower than the reference value, that is, only when a result of the calculation of the number of particles attached to the substrate is equal to or less than a predetermined specified value. Accordingly, even though the particle test actually using a substrate is not conducted, the particle concentration in the chamber 65 can be lowered to a level at which the particle test can be passed.

Furthermore, in the heat treatment apparatus according to this preferred embodiment having the above-described configuration, the outlet passage 93 that exhausts the measurement part 50 is provided. This can more smoothly introduce the gas existing in the chamber 65 into the measurement chamber of the measurement part 50.

Furthermore, in the heat treatment apparatus according to this preferred embodiment having the above-described configuration, the inside diameter of the outlet passage 93 that exhausts the measurement part 50 is smaller than the inside diameters of the outlet passages 79 and 84 that exhaust the interior of the chamber 65. Accordingly, a back flow of the gas from the outlet passage 93 toward the measurement part 50 is not likely to occur. Thus, the accuracy of measurement of the air particle concentration is further improved.

Furthermore, in the heat treatment apparatus according to this preferred embodiment having the above-described configuration, the flash lamps 69 are provided, and the flash lamps 69 emit a light flash to the substrate received in the chamber 65 to thereby heat-treat the received substrate. In a case of adopting a light flash of flash lamps, a large impact is given to the substrate during the heat treatment and therefore cracking of the substrate is likely to occur. As a result, the frequency of the maintenance increases. However, in the heat treatment apparatus according to this preferred embodiment, the measurement part 50 measures the air particle concentration. This makes it easy to examine a result of the cleaning performed in the start-up process that follows the maintenance. Accordingly, even if the frequency of the maintenance increases due to the emission of flashes of light, a cost increase in the start-up process can be suppressed as compared with a case of not using the air particle concentration.

Furthermore, in the heat treatment apparatus according to this preferred embodiment having the above-described configuration, air particles in the processing space of the chamber 65 are removed by using a combination of the light source 5 including the flash lamps 69 and the like with the supply and exhaust system. This enables the air particle concentration in the processing space of the chamber 65 to be lowered to a level at which the particle test can be passed.

Second Preferred Embodiment

Next, a second preferred embodiment of the present invention will be described. A configuration of a heat treatment apparatus according to the second preferred embodiment is completely the same as that of the first preferred embodiment. In the first preferred embodiment, after the maintenance operation, the air particle concentration is measured and the cleaning process for cleaning the chamber 65 is performed. In the second preferred embodiment, on the other hand, the air particle concentration is measured during the heat treatment being performed on the semiconductor wafer W, and a cleaning process as needed is performed. Specifically, in the heat treatment apparatus according to the present invention, the measurement part 50 that measures an air particle concentration is attached to the chamber 65, to enable the air particle concentration in the chamber 65 to be measured as needed even during a process being performed on the semiconductor wafer W. Therefore, in the second preferred embodiment, the air particle concentration in the chamber 65 is measured during a steady process being performed on the semiconductor wafer W, and particle removal process in accordance with an obtained concentration level is performed.

FIG. 8 is a flowchart showing a process in the heat treatment apparatus according to the second preferred embodiment. Firstly, the air particle concentration is measured during a process being performed on the semiconductor wafer W (step S30). Details of the heat treatment performed on the semiconductor wafer W in the heat treatment apparatus are as described in the first preferred embodiment. That is, the flash heating is performed using the flash lamps 69 emitting a light flash to the surface of the semiconductor wafer W that has been held in the chamber 65 and preheated by the heating plate 74 and the susceptor 73.

At any timing during such a steady heat treatment being performed on the semiconductor wafer W, the measurement part 50 measures the air particle concentration in the processing space of the chamber 65. The particle size (particle diameter) for which the measurement part 50 performs the measurement during the process can be set to any appropriate value. A result of the measurement by the measurement part 50 is transmitted to the controller 10.

Figure 10:
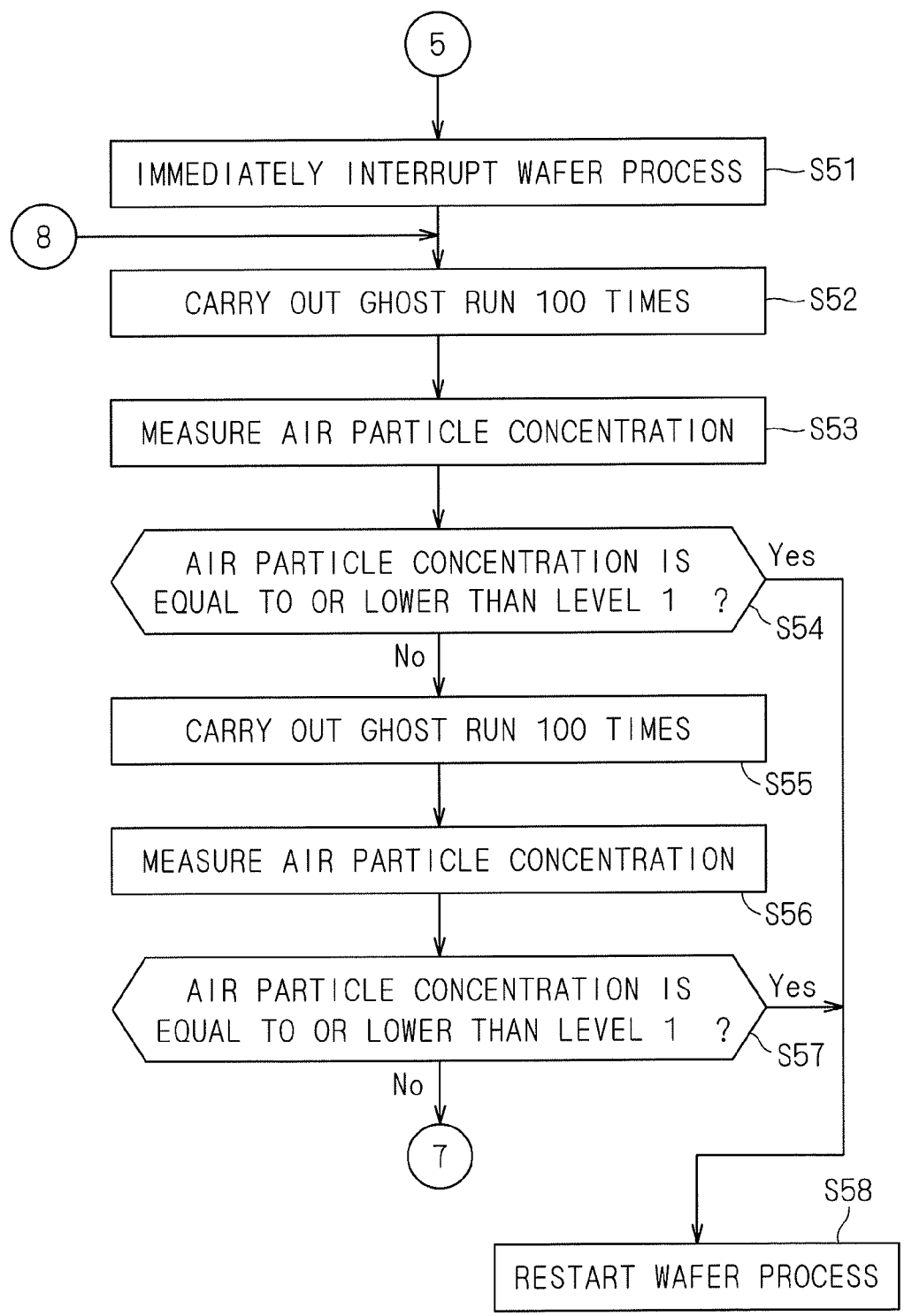
FIG. 10 is a flowchart showing procedures taken when the air particle concentration exceeds a level 2.
Figure 11:
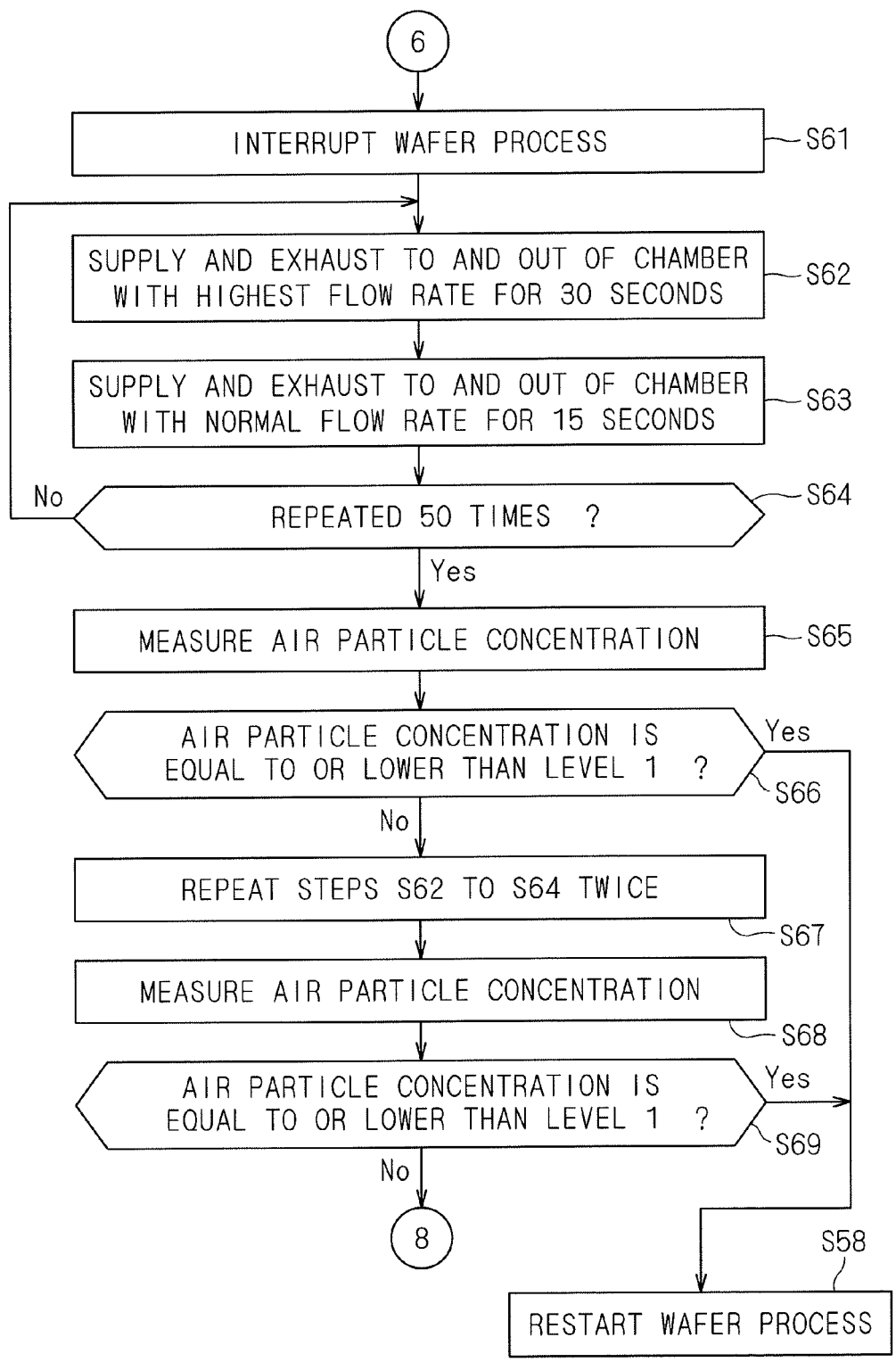
FIG. 11 is a flowchart showing procedures taken when the air particle concentration exceeds a level 1.

In the second preferred embodiment, three levels of threshold values are set for the air particle concentration during the wafer process, and processing in accordance with the concentration level is performed. To be specific, when the air particle concentration during the wafer process exceeds a level 3 (third threshold value), a process shown in a flowchart of FIG. 9 is performed (step S40). When the air particle concentration is equal to or lower than the level 3 and exceeds a level 2 (second threshold value), a process shown in a flowchart of FIG. 10 is performed (step S50). When the air particle concentration is equal to or lower than the level 2 and exceeds a level 1 (first threshold value), a process shown in a flowchart of FIG. 11 is performed (step S60).

Here, the level 1, which is the first threshold value for determining the air particle concentration, indicates an air particle concentration corresponding to a situation where the number of particles attached to one wafer increases by 25 to 50 when comparing before and after the heat-treatment of the semiconductor wafer W in the heat treatment apparatus. The level 2, which is the second threshold value for measuring the air particle concentration, is an air particle concentration corresponding to a situation where the number of particles attached to one wafer increases by 51 to 100 when comparing before and after the heat treatment of the semiconductor wafer W. The level 3, which is the third threshold value for measuring the air particle concentration, is an air particle concentration corresponding to a situation where the number of particles attached to one wafer increases by 101 or more when comparing before and after the heat treatment of the semiconductor wafer W.

Figure 12:
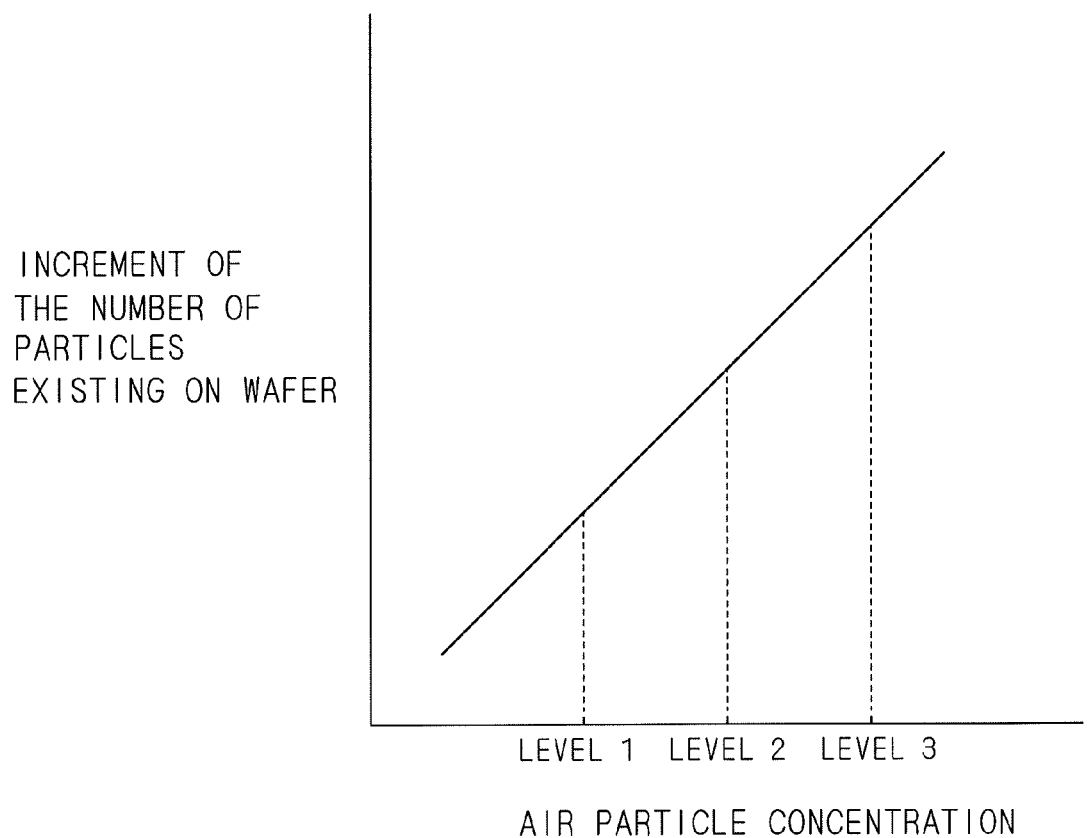
FIG. 12 shows the correlation between the increment of the number of particles on a semiconductor wafer and the air particle concentration before and after a process.

FIG. 12 shows the correlation between the increment of the number of particles existing on the semiconductor wafer W and the air particle concentration before and after the process. The meaning of FIG. 12 is similar to the meaning of FIG. 4. The increment of the number of particles existing on the wafer is generally proportional to the air particle concentration. The level 3, which corresponds to a situation where the increment of the number of particles is large, is higher than the level 2, and the level 2 is higher than the level 1. Based on a result of the measurement by the measurement part 50, the controller 10 determines which of the levels the air particle concentration in the wafer process is found at. Then, for example, the controller 10 causes the result of the determination to be displayed on the display part 21 (FIG. 3). Then, based on contents thus displayed, processing in accordance with the level of the air particle concentration is performed.

For convenience of the description, procedures taken when it is determined in step S60 that the air particle concentration is equal to or lower than the level 2 and exceeds the level 1 will be described in the first place. FIG. 11 is a flowchart showing procedures taken when the air particle concentration exceeds the level 1. A situation where the air particle concentration is equal to or lower than the level 2 and exceeds the level 1 is a situation where minor contamination with particles occurs in the chamber 65. When such minor contamination occurs, the particles existing in the chamber 65 are removed with a maximum flow rate of the supply and exhaust to and out of the chamber 65. Hereinafter, a specific description will be given to the procedures therefor.

Firstly, when it is determined that the air particle concentration is equal to or lower than the level 2 and exceeds the level 1, the process of the semiconductor wafer W is interrupted (step S61). Here, the process of the semiconductor wafer W being treated in the heat treatment apparatus is not immediately interrupted, but the process is interrupted at a good timing which comes when a certain section of the process is completed. For example, the process is interrupted after the treatment of the final semiconductor wafer W of a lot including the currently treated semiconductor wafer W is completed.

After the wafer process is interrupted, supply and exhaust to and out of the chamber 65 are performed with the highest flow rate for 30 seconds (step S62). To be specific, by means of the mass flow controller 89 provided in the gas pipe 82, the flow rate of the nitrogen gas supplied to the chamber 65 is set to be the highest flow rate (for example, corresponding to 50 liters/min). At the same time, an exhaust path for exhausting the chamber 65 is switched to the large-diameter pipe of the exhaust pipe 83, and the chamber 65 is exhausted with the highest flow rate.

After such supply and exhaust to and out of the chamber 65 with the highest flow rate are performed for 30 seconds, supply and exhaust to and out of the chamber 65 with a normal flow rate are performed for 15 seconds (step S63). More specifically, by means of the mass flow controller 89, the flow rate of the nitrogen gas supplied to the chamber 65 is set to be the flow rate (for example, 20 liters/min) adopted in a normal wafer process, and the exhaust path is switched to the small-diameter pipe of the exhaust pipe 83. Thus, the chamber 65 is exhausted with the normal flow rate.

The supply and exhaust (30 seconds) with the highest flow rate in step S62 and the supply and exhaust (15 seconds) with the normal flow rate in step S63 are repeated 50 times (step S64). Repeating the supply and exhaust with the highest flow rate and the supply and exhaust with the normal flow rate in this manner allows the particles remaining in the chamber 65 to be discharged to the outside of the chamber 65. A length of time of the supply and exhaust with the highest flow rate, a length of time of the supply and exhaust with the normal flow rate, and the number of times they are repeated, are merely illustrative, and their values are not limited to the illustrated ones.

Then, the measurement part 50 measures the air particle concentration in the chamber 65 (step S65). When a result of the measurement by the measurement part 50 indicates that the air particle concentration is equal to or lower than the above-mentioned level 1, the process proceeds from step S66 to step S58, in which the process of the semiconductor wafer W in the heat treatment apparatus is restarted.

On the other hand, when the air particle concentration still exceeds the level 1 even after particles are removed by the repetition of the supply and exhaust with the highest flow rate and the supply and exhaust with the normal flow rate, the process of steps S62 to S64 is additionally repeated twice (step S67). That is, a process in which the supply and exhaust with the highest flow rate and the supply and exhaust with the normal flow rate are repeated 50 times is performed twice. It should be noted that the number of times of the repetition in step S67 is not limited to twice, and it may be once or three times.

Then, the measurement part 50 measures the air particle concentration in the chamber 65 again (step S68). When, as a result of the re-measurement, the air particle concentration is equal to or lower than the level 1, the process proceeds from step S69 to step S58, in which the process of the semiconductor wafer W in the heat treatment apparatus is restarted. On the other hand, when the air particle concentration still exceeds the level 1, a particle removal process corresponding to the level 2 is performed, as follows.

FIG. 10 is a flowchart showing procedures taken when the air particle concentration exceeds the level 2 in step S50 of FIG. 8. A situation where the air particle concentration is equal to or lower than the level 3 and exceeds the level 2 is a situation where a medium degree of contamination with particles occurs in the chamber 65. When such a medium degree of contamination occurs, "ghost run" is carried out to remove particles existing in the chamber 65.

Firstly, when it is determined that the air particle concentration is equal to or lower than the level 3 and exceeds the level 2, the process of the semiconductor wafer W is immediately interrupted (step S51). More specifically, the semiconductor wafer W that is currently processed is continued to be processed, but transport of any new semiconductor wafer W into the heat treatment apparatus is stopped. When the contamination in the chamber 65 is minor (when the air particle concentration is equal to or lower than the level 2 and exceeds the level 1), the continuation of the process is barely allowed. However, when the contamination is at the medium degree (when the air particle concentration is equal to or lower than the level 3 and exceeds the level 2), the continuation of the process involves a high risk of producing a fault wafer. Therefore, the process is immediately interrupted.

After the wafer process is immediately interrupted, the ghost run is carried out 100 times (step S52). Also when it is determined in step S69 of FIG. 11 that the air particle concentration exceeds the level 1, the process proceeds to step S52, in which the ghost run is carried out 100 times. Here, the "ghost run" means a process in which the flash lamps 69 are turned on under a nitrogen atmosphere while the transport robot, the gate valve 68, the heating plate 74, and the like, are operated as if a wafer was transported into the chamber 65. The "ghost run" is the same process as the process performed in step S150 of FIG. 5. To be specific, although there is actually no semiconductor wafer W, a semiconductor wafer W is imaginarily transported and the imaginary semiconductor wafer W is processed to discharge particles from the chamber 65. Carrying out such ghost run 100 times allows particles remaining in the chamber 65 to be removed. The number of times the ghost run is carried out is not limited to 100 times, and it may be any appropriate number of times.

Then, the measurement part 50 measures the air particle concentration in the chamber 65 (step S53). When a result of the measurement by the measurement part 50 indicates that the air particle concentration is equal to or lower than the above-mentioned level 1, the process proceeds from step S54 to step S58, in which the process of the semiconductor wafer W in the heat treatment apparatus is restarted.

On the other hand, when the air particle concentration still exceeds the level 1 even after particles are removed by the ghost run, the ghost run is carried out 100 times again (step S55). The number of times the ghost run is carried out in step S55 is also not limited to 100 times, and it may be any appropriate number of times.

Then, the measurement part 50 measures the air particle concentration in the chamber 65 again (step S56). When, as a result of the re-measurement, the air particle concentration is equal to or lower than the level 1, the process proceeds from step S57 to step S58, in which the process of the semiconductor wafer W in the heat treatment apparatus is restarted. On the other hand, when the air particle concentration still exceeds the level 1, a particle removal process corresponding to the level 3 is performed, as follows.

FIG. 9 is a flowchart showing procedures taken when the air particle concentration exceeds the level 3 in step S40 of FIG. 8. A situation where the air particle concentration exceeds the level 3 is a situation where major contamination with particles occurs in the chamber 65. When such major contamination occurs, it is necessary to open the chamber 65 and carry out the maintenance. Here, in some cases, when the air particle concentration is measured during the wafer process in step S30 of FIG. 8, the air particle concentration suddenly exceeds the level 2 or the level 3. One conceivable reason therefor is that the semiconductor wafer W brings particles into the chamber 65 or a trouble occurs in the gas supply and exhaust system for supplying and exhausting a gas to and out of the chamber 65.

When it is determined that the air particle concentration exceeds the level 3, the process of the semiconductor wafer W is immediately interrupted (step S41). This is the same as the immediate interruption shown in FIG. 10. That is, the semiconductor wafer W that is currently processed is continued to be processed, but transport of any new semiconductor wafer W into the heat treatment apparatus is stopped. The contamination in the chamber 65 is major (when the air particle concentration exceeds the level 3), the continuation of the process involves an extremely high risk of producing a fault wafer. Therefore, the process is immediately interrupted.

After the wafer process is immediately interrupted, the chamber 65 is opened and the maintenance is carried out (step S42). Also when it is determined in step S57 of FIG. 10 that the air particle concentration exceeds the level 1, the process proceeds to step S42, in which the maintenance is carried out. This maintenance step is the same as step S110 of FIG. 5. After the maintenance, a process that follows the maintenance is performed (step S43). The process that follows the maintenance is the same as that performed in steps S120 to S210 of the first preferred embodiment shown in FIGS. 5 and 6. That is, in consideration of a result of the measurement of the air particle concentration by the measurement part 50, an actual particle test is conducted.

In this manner, in the second preferred embodiment, the measurement part 50 measures the air particle concentration during the heat treatment being performed on the semiconductor wafer W, and a particle removal in accordance with the concentration level is performed. In the heat treatment apparatus according to the present invention, the measurement part 50 that measures an air particle concentration is attached to the chamber 65, to enable the air particle concentration in the chamber 65 to be measured as needed even during a process being performed on the semiconductor wafer W. When the particle concentration obtained as a result of the measurement exceeds the predetermined threshold value, particles existing in the chamber 65 are removed. Accordingly, even when the particle concentration in the chamber 65 increases during the process of the semiconductor wafer W, the number of particles can be promptly reduced.

When the air particle concentration obtained as a result of the measurement during the wafer process is equal to or lower than the level 3 (when a status of contamination in the chamber 65 is at a minor or medium degree), the particle removal process is performed without opening the chamber 65. This can reduce a downtime of the heat treatment apparatus.

<Modifications>

While the present invention has been shown and described in detail, the foregoing description is in all aspects illustrative and not restrictive. Therefore, in the preferred embodiments of the present invention, modifications and omissions can be appropriately given within the scope of the invention. For example, the usefulness of the present invention is not impaired even when the present invention directed to the measurement of an air particle concentration is applied to an apparatus, such as an RTP apparatus or a single-wafer type CVD apparatus, that performs the heat treatment using something other than flash lamps. Moreover, although the heat treatment apparatus according to this preferred embodiment preheats a substrate by means of a heating plate at a time of the heat treatment, the preheating may be performed by using heat radiated from halogen lamps or the like.

In the first preferred embodiment, it may be acceptable that a wafer is transported about 50 times in a time period between step S150 and step S160. At this time, a dummy wafer is transported in accordance with a normal process flow, and received in the chamber 65. As for the flash heating, for example, the flash heating is performed in 25-times transports among the 50-times transports, and not performed in the remaining 25-times transports. Transporting the dummy wafer into and out of the chamber 65 causes particles remaining in the chamber 65 to be attached to the dummy wafer and thus brought out. As a result, the particle removal effect is further enhanced. In performing the particle removal by means of such wafer transports, it is preferable to use a new dummy wafer each time.

Furthermore, after the ghost run is performed in the second preferred embodiment (after step S52 and step S55), too, the wafer transport may be carried out about 50 times to enhance the particle removal effect.

While the invention has been described in detail, the foregoing description is in all aspects illustrative and not restrictive. It is understood that numerous other modifications and variations can be devised without departing from the scope of the invention.

What is claimed is:

1. A heat treatment apparatus for heating a substrate, comprising:
   a process chamber for receiving a substrate therein; and
   a measurement part for introducing a gas in a processing space provided in said process chamber and measuring an air particle concentration in the gas;
   a first exhaust part for exhausting said measurement part; and
   a second exhaust part for exhausting said process chamber via a path different from said measurement part and said first exhaust part;
   wherein, the inside diameter of said first exhaust part is smaller than the inside diameter of said second exhaust part.

2. The heat treatment apparatus according to claim 1, further comprising:

a storage part for storing correlation information that indicates the correlation between an air particle concentration in said processing space and a number of particles attached to a substrate received in said process chamber; and a calculation part for calculating, based on a result of the measurement by said measurement part and said correlation information, a number of particles that will be attached to a substrate intended to be received in said process chamber.

3. The heat treatment apparatus according to claim 1, further comprising a flash lamp for heating a substrate received in said process chamber by emitting a light flash to said substrate.

4. The heat treatment apparatus according to claim 1, further comprising a removal part for removing air particles existing in said processing space provided in said process chamber.

* * * * *